US00PP31328P2

(12) United States Plant Patent
Valin

(10) Patent No.: US PP31,328 P2
(45) Date of Patent: Jan. 7, 2020

(54) ***BEGONIA* PLANT NAMED 'TMBG1307'**

(50) Latin Name: ***Begonia* x *tuberhybrida***
Varietal Denomination: TMBG1307

(71) Applicant: Charles Valin, Ipswich (GB)

(72) Inventor: Charles Valin, Ipswich (GB)

(73) Assignee: Branded Garden Products Ltd., Ipswich, Suffolk (GB)

( * ) Notice: Subject to any disclaimer, the term of this patent is extended or adjusted under 35 U.S.C. 154(b) by 0 days.

(21) Appl. No.: 16/350,434

(22) Filed: Nov. 15, 2018

(51) Int. Cl.
*A01H 5/02* (2018.01)
*A01H 6/18* (2018.01)

(52) U.S. Cl.
USPC ..... Plt./343
CPC ..... *A01H 6/185* (2018.05)

(58) Field of Classification Search
USPC ..... Plt./343
See application file for complete search history.

(56) References Cited

PUBLICATIONS

UPOV hit on *Begonia* plant named, 'TMBG1307', QZ PBR 2669, filed Oct. 23, 2018.*

* cited by examiner

*Primary Examiner* — Anne Marie Grunberg
(74) *Attorney, Agent, or Firm* — C. A. Whealy

(57) ABSTRACT

A new and distinct cultivar of *Begonia* plant named 'TMBG1307', characterized by its upright to spreading and mounded plant habit; dark green to dark greyed green-colored leaves; freely and continuously flowering habit; strongly fragrant flowers; and large ruffled double-type flowers that are bright orange in color.

3 Drawing Sheets

Botanical designation: *Begonia* x *tuberhybrida*.
Cultivar denomination: 'TMBG1307'.

BACKGROUND OF THE INVENTION

The present invention relates to a new and distinct cultivar of *Begonia* plant, botanically known as *Begonia* x *tuberhybrida*, and hereinafter referred to by the name 'TMBG1307'.

The new *Begonia* plant is a product of a planned breeding program conducted by the Inventor in Harkstead, Ipswich, United Kingdom. The objective of the breeding program was to develop new trailing *Begonia* plants with fragrant flowers.

The new *Begonia* plant originated from a cross-pollination made by the Inventor in August, 2010 of a proprietary selection of *Begonia* x *tuberhybrida* identified as code number 260, not patented, as the female, or seed, parent and a proprietary selection of *Begonia* x *tuberhybrida* identified as code number 146, not patented, as the male, or pollen, parent. The new *Begonia* plant was discovered and selected by the Inventor as a single flowering plant from within the progeny of the stated cross-pollination in a controlled greenhouse environment in Harkstead, Ipswich, United Kingdom in July, 2011.

Asexual reproduction of the new *Begonia* plant by shoot tip cuttings in a controlled greenhouse environment in Harkstead, Ipswich, United Kingdom since August, 2012 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'TMBG1307'. These characteristics in combination distinguish 'TMBG1307' as a new and distinct *Begonia* plant:

1. Upright to spreading and mounded plant habit.
2. Dark green to dark greyed green-colored leaves.
3. Freely and continuously flowering habit.
4. Strongly fragrant flowers.
5. Large ruffled double-type flowers that are bright orange in color.

Plants of the new *Begonia* can be compared to plants of the female parent selection. Plants of the new *Begonia* differ from plants of the female parent selection in the following characteristics:

1. Flowers of plants of the new *Begonia* are more outwardly facing than and not as upright as flowers of plants of the female parent selection.
2. Flowers of plants of the new *Begonia* are more fragrant than flowers of plants of the female parent selection.
3. Flowers of plants of the new *Begonia* are bright orange in color whereas flowers of plants of the female parent selection are deep salmon in color.

Plants of the new *Begonia* can be compared to plants of the male parent selection. Plants of the new *Begonia* differ from plants of the male parent selection in the following characteristics:

1. Leaves of plants of the new *Begonia* are darker in color than leaves of plants of the male parent selection.
2. Flowers of plants of the new *Begonia* are smaller than flowers of plants of the male parent selection.

3. Flowers of plants of the new *Begonia* are bright orange in color whereas flowers of plants of the male parent selection are red in color.

Plants of the new *Begonia* can also be compared to plants of the *Begonia pendula* 'Victoria Falls', disclosed in U.S. Plant Pat. No. 20,653. In side-by-side comparisons, plants of the new *Begonia* differ from plants of 'Victoria Falls' in the following characteristics:

1. Leaves of plants of the new *Begonia* are darker in color than leaves of plants of 'Victoria Falls'.
2. Flowers of plants of the new *Begonia* are twice as large as flowers of plants of 'Victoria Falls'.
3. Flowers of plants of the new *Begonia* are strongly fragrant whereas flowers of plants of 'Victoria Falls' are not fragrant.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'TMBG1307' grown in a container.

The photograph on the second sheet is a close up view of upper surfaces of a typical leaf, a typical flower bud, a typical developing flower and a typical fully developed flower of 'TMBG1307'.

The photograph on the third sheet is a close up view of lower surfaces of a typical leaf, a typical flower bud, a typical developing flower and a typical fully developed flower of 'TMBG1307'.

DETAILED BOTANICAL DESCRIPTIONS

Plants used for the aforementioned photographs and following observations and measurements were grown in 11-cm containers during the spring in a glass-covered greenhouse in Maasdijk, The Netherlands. During the production of the plants, day and night temperatures ranged from 19° C. to 21° C. Plants were nine weeks old when the photographs and the description were taken. In the following description, color references are made to The Royal Horticultural Society Colour Chart, 2015 Edition, except where general terms of ordinary dictionary significance are used.

Botanical Classification: *Begonia* x *tuberhybrida* 'TMBG1307'.

Parentage:

*Female, or seed, parent.*—Proprietary selection of *Begonia* x *tuberhybrida* identified as code number 260, not patented.

*Male, or pollen, parent.*—Proprietary selection of *Begonia* x *tuberhybrida* identified as code number 146, not patented.

Propagation:

*Type: By shoot tip cuttings.*

*Time to initiate roots, summer.*—About one week at temperatures about 20° C. to 25° C.

*Time to initiate roots, winter.*—About one week at temperatures about 18° C. to 20° C.

*Time to produce a rooted young plant, summer.*—About 34 days at temperatures about 20° C. to 25° C.

*Time to produce a rooted young plant, winter.*—About 36 days at temperatures about 18° C. to 20° C.

*Root description.*—Thin, fibrous; typically light brown in color, actual color of the roots is dependent on substrate composition, water quality, fertilizer type and formulation, substrate temperature and physiological age of roots; plants of the new *Begonia* have not been observed to form tubers.

*Rooting habit.*—Moderately freely branching; medium density.

Plant Description:

*Plant form and growth habit.*—Upright to spreading and mounded plant habit; flattened globular in shape; sparsely branching habit; low vigor to moderately vigorous growth habit.

*Plant height, soil level to top of foliar plane.*—About 11.8 cm.

*Plant height, soil level to top of floral plane.*—About 12 cm.

*Plant width.*—About 23.2 cm.

*Lateral branch description.*—Length: About 4.3 cm. Diameter: About 1 cm. Internode length: About 6 mm. Aspect: About 25° from vertical. Strength: Moderately strong. Texture: Sparsely pubescent. Color, developed: Close to between 199C and N199C. Color, developed: Close to 152B strongly tinged with close to 177A to 177B.

*Leaf description.*—Arrangement: Alternate, simple. Length: About 14.5 cm. Width: About 7.7 cm. Shape: Ovate. Apex: Acute. Base: Oblique, moderately imbricate. Margin: Crenate to serrulate; moderately to strongly undulate. Texture and luster, upper and lower surfaces: Moderately pubescent; velvety; moderately glossy. Venation pattern: Palmate; reticulate. Color: Developing leaves, upper surface: Close to 200A and 200B; venation, close to 144A. Developing leaves, lower surface: Close to 183B; venation, close to 152A to 152B. Fully expanded leaves, upper surface: Much darker than between 139A and N189A; venation, close to NN137B. Fully expanded leaves, lower surface: Close to 183B; venation, close to 148A. Petioles: Length: About 3.4 cm. Diameter: About 5 mm. Strength: Low, flexible. Texture and luster, upper and lower surfaces: Densely pubescent; slightly glossy. Color, upper and lower surfaces: Close to 152B; distally, close to 178A.

*Stipules.*—Quantity and arrangement: Two at each leaf axils. Length: Close to 1.5 cm. Width: Close to 1.2 cm. Shape: Broadly ovate. Apex: Broadly acute. Base: Broadly cuneate. Margins: Entire. Texture, upper and lower surfaces: Smooth, glabrous. Color, upper surface: Close to 173B to 173D. Color, lower surface: Close to 173A to 173D.

Flower Description:

*Flowering habit.*—Double-type (male) rotate flowers and occasional single-type (female) rotate flowers arranged in axillary cymes; freely flowering habit with about three flowers per cyme and about 30 flowers developing per plant; flowers face mostly outwardly to slightly upright.

*Fragrance.*—Strongly fragrant; fragrance pleasant, sweetly acidic; similar to rose and citrus.

*Natural flowering season.*—Plants begin flowering about six weeks after planting; long flowering period, in the garden plants flower freely and continuously from spring until autumn in The Netherlands and plants can be flowered year-round in greenhouses.

*Flower longevity.*—Individual flowers last about ten days on the plant; flowers not persistent.

*Inflorescence height* (*excluding peduncle*).—About 7.6 cm.

*Inflorescence diameter.*—About 11.4 cm.

*Flower buds.*—Length: About 3.5 cm. Diameter: About 1.5 cm to 4 cm. Shape: Reniform to nearly circular, flattened. Texture and luster: Smooth, glabrous; velvety; slightly glossy. Color: Close to 34B fading proximally to close to 34D.

*Female flowers, diameter.*—About 6.3 cm.

*Female flowers, depth* (*height*).—About 3.9 cm.

*Female flowers, tepals.*—Quantity and arrangement: Typically five per flower arranged in about two whorls. Length: About 3.5 cm. Width: About 4.1 cm. Shape: Reniform to broadly obovate. Apex: Praemorse to irregularly dentate. Base: Cordate. Margin: Irregularly dentate; slightly undulate. Texture and luster, upper surface: Smooth, glabrous; moderately velvety; matte. Texture and luster, lower surface: Smooth, glabrous; slightly velvety; slightly glossy. Color: When opening, upper surface: Close to N30B fading proximally to close to 30B. When opening, lower surface: Close to 33A to 33B. Fully opened, upper surface: Close to 33A to 33B; venation, close to 33A to 33B; color does not fade with development. Fully opened, lower surface: Close 33B fading proximally to close to 29A; venation, close to N170B and N170C; color does not fade with development.

*Female flowers, tepaloids.*—Female flowers are single; no tepaloid development has been observed on female flowers of plants of the new *Begonia.*

*Male flowers, diameter.*—About 9.4 cm.

*Male flowers, depth* (*height*).—About 4 cm.

*Male flowers, tepals.*—Quantity and arrangement: Typically two per flower, opposite, in a single whorl. Length: About 5.1 cm. Width: About 7.4 cm. Shape: Reniform to broadly obovate. Apex: Praemorse to irregularly dentate. Base: Cordate. Margin: Irregularly dentate; slightly undulate. Texture and luster, upper and lower surfaces: Smooth, glabrous; moderately velvety; matte. Color: When opening, upper surface: Close to 30A fading proximally to close to 30D. When opening, lower surface: Close to N30A fading proximally to close to N30B. Fully opened, upper surface: Close to 33A to 33D; venation, close to 33A to 33D; color does not fade with development. Fully opened, lower surface: Close 30A fading proximally to close to 29A to 29B; venation, close to N170B and. N170C; color does not fade with development.

*Male flowers, tepaloids.*—Quantity and arrangement: Typically about 50 per flower in concentric central whorls. Length: About 1.5 cm to 4.7 cm. Width: About 1.2 cm to 6.7 cm. Shape: Broadly obovate to nearly reniform. Apex: Obtuse. Base: Broadly attenuate. Margin: Entire to shallowly crenate; moderately undulate. Texture and luster, upper and lower surfaces: Smooth, glabrous; velvety; matte. Color: When opening, upper surface: Close to 32A to 32C. When opening, lower surface: Close to 32A to 32D. Fully opened, upper surface: Close to 32C; venation, close to 32C; color does not fade with development. Fully opened, lower surface: Close to 33C; venation, close to N170C; color does not fade with development.

*Peduncles, female and male flowers.*—Length: About 6.4 cm. Diameter: About 6 mm. Angle: About 50° from stem axis. Strength: Moderately strong, flexible. Texture and luster: Sparsely pubescent; glossy. Color: Close to 152B to 152C; distally, close to146A to 146B.

*Pedicels, female and male flowers.*—Length: About 3.1 cm. Diameter: About 4 mm to 5.5 mm. Aspect: About 35° from peduncle axis. Strength: Moderately strong. Texture and luster: Sparsely pubescent; glossy. Color: Close to 151A to 151B; upper surface tinged with close to 169C to 169D.

*Reproductive organs.*—Stamens: None observed; all stamens on male flowers transformed into tepaloids. Pistils: Observed on female flowers only. Quantity: Four per flower. Pistil length: About 1 cm. Stigma diameter: About 8 mm. Stigma shape: Cleft. Stigma color: Close to 14A to 14B. Style length: About 5 mm. Style color: Close to 11A. Ovary color: Close to 144B to 144D; upper surface tinged with close to 171A; wing, close to N34A and 179A.

*Flower bracts, female and male flowers.*—Quantity and arrangement: Two per flower, opposite, at peduncle and flower attachment. Length: About 2.3 cm. Width: About 3.5 cm. Shape: Reniform. Apex: Rounded. Base: Cordate. Margins: Finely ciliate. Texture and luster, upper and lower surfaces: Smooth, glabrous; moderately glossy. Color, upper surface: Close to 145A tinged with close to 35A. Color, lower surface: Close to N144C.

*Seeds and fruits.*—To date, seed and fruit production have not been observed on plants of the new *Begonia.*

Disease & Pest Resistance: To date, resistance to pathogens and pests common to *Begonia* plants has not been observed on plants of the new *Begonia.*

Temperature Tolerance: Plants of the new *Begonia* have been observed to tolerate high temperatures about 35° C. and to be suitable for USDA Hardiness Zones 10 to 12.

It is claimed:

1. A new and distinct *Begonia* plant named 'TMBG1307' as illustrated and described.

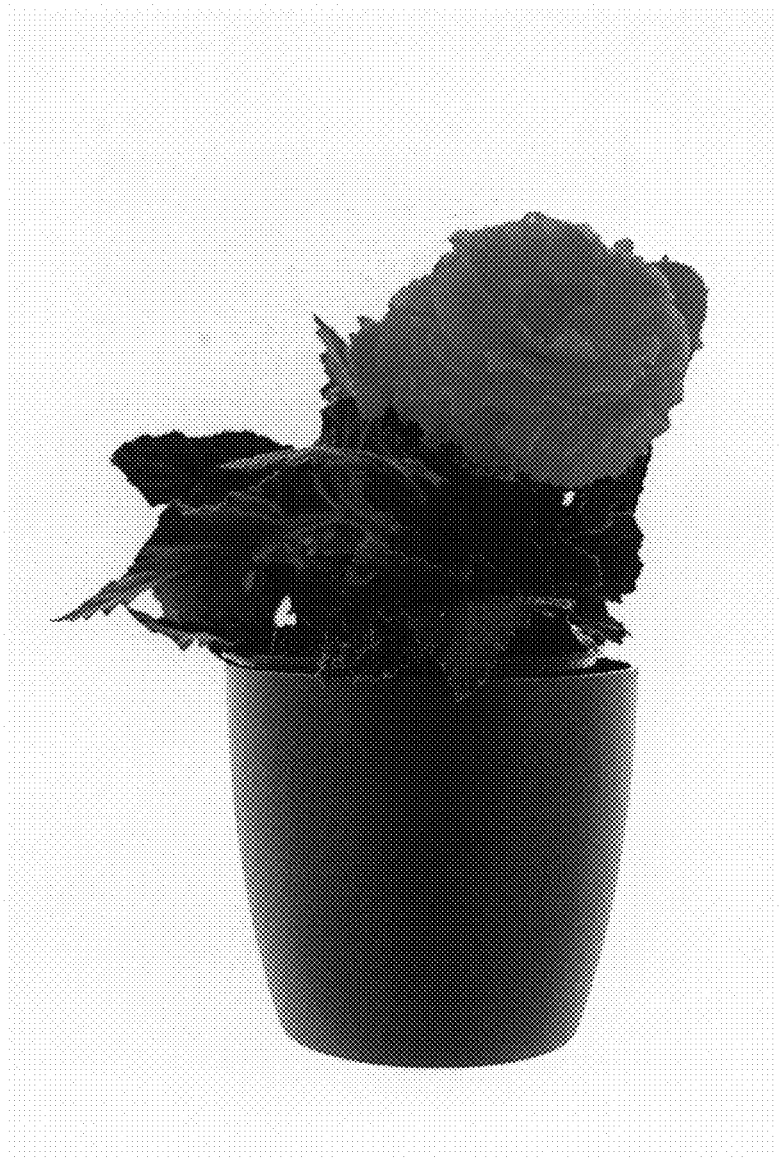

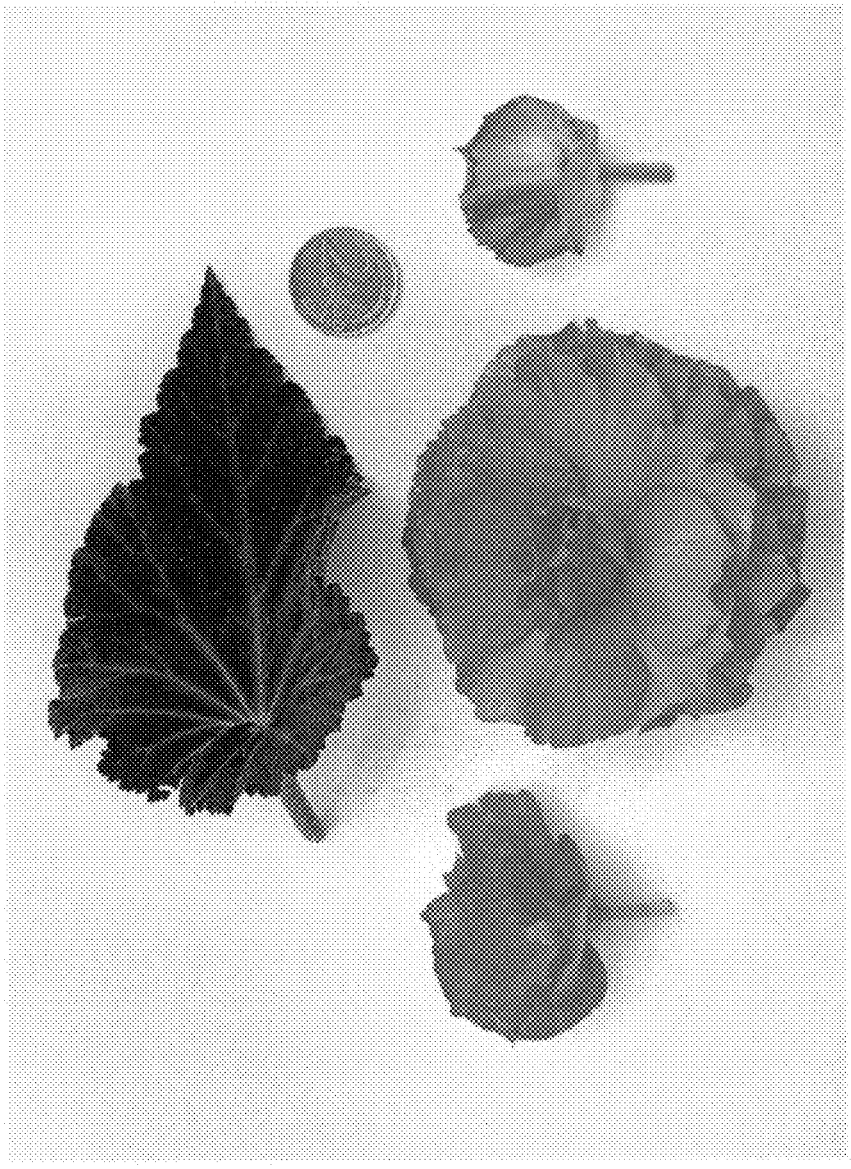

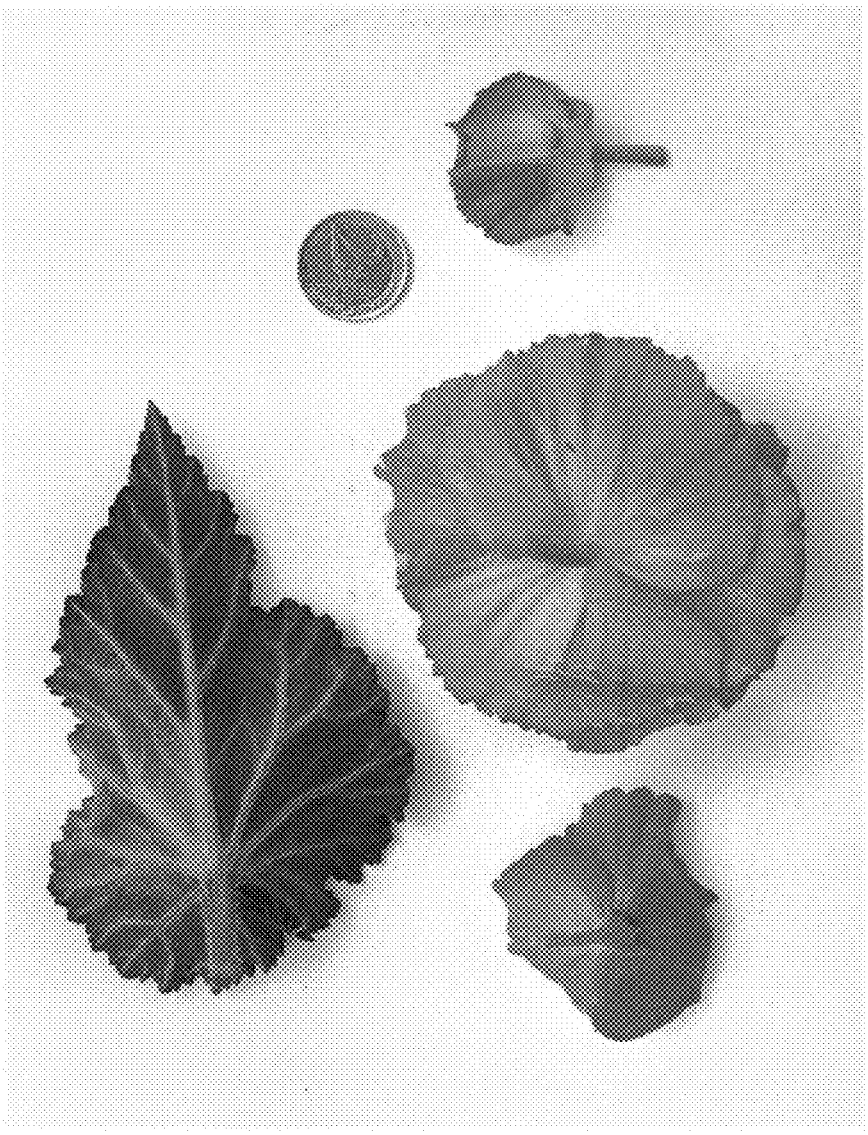

* * * * *